United States Patent [19]

Shah et al.

[11] Patent Number: 5,536,563

[45] Date of Patent: Jul. 16, 1996

[54] NONWOVEN ELASTOMERIC MATERIAL

[75] Inventors: Ketan N. Shah, Appleton; John P. Cundy, Oshkosh, both of Wis.

[73] Assignee: Kimberly-Clark Corporation, Neenah, Wis.

[21] Appl. No.: 348,549

[22] Filed: Dec. 1, 1994

[51] Int. Cl.$^6$ .............................. C08L 53/00; D03D 3/00
[52] U.S. Cl. .................... 428/224; 428/284; 428/364; 428/903; 428/913; 525/97; 525/98; 525/99
[58] Field of Search .................................. 525/97, 98, 99; 428/224, 903, 284, 364, 913

[56] References Cited

U.S. PATENT DOCUMENTS

| | | | |
|---|---|---|---|
| 4,259,220 | 3/1981 | Bunnelle et al. | 260/27 BB |
| 4,418,123 | 11/1983 | Burnelle et al. | 428/517 |
| 4,789,699 | 12/1988 | Kieffer et al. | 524/271 |
| 5,085,655 | 2/1992 | Mann et al. | 604/389 |

FOREIGN PATENT DOCUMENTS

| | | |
|---|---|---|
| 0428017A2 | 5/1991 | European Pat. Off. |
| WO80/00029 | 1/1980 | WIPO |
| WO91/15364 | 10/1991 | WIPO |
| WO94/26834 | 11/1994 | WIPO |

Primary Examiner—James J. Bell
Attorney, Agent, or Firm—John R. Schenian

[57] ABSTRACT

Disclosed is a nonwoven elastomeric material of a thermoplastic, elastomeric composition comprising a block copolymer which comprises an elastomeric midblock portion and a thermoplastic endblock portion, a first tackifying resin substantially compatible with and substantially associated with the midblock portion, and a second tackifying resin substantially compatible with and substantially associated with the endblock portion. The nonwoven elastomeric material exhibits both desired elastic and adhesive properties and is useful in imparting elastic properties to flexible, non-elastic substrates. Also disclosed is a disposable absorbent product, including the nonwoven elastomeric material and intended for the absorption of body fluids.

26 Claims, 2 Drawing Sheets

NONWOVEN ELASTOMERIC MATERIAL

BACKGROUND OF THE INVENTION

1. Field of the Invention

The present invention relates to a nonwoven elastomeric material which may be used to impart elastic properties to flexible, non-elastic substrates.

2. Description of the Related Art

Vulcanized rubber or synthetic rubber elastic bands or threads have typically been used to provide elastic properties to flexible substrates by attaching the elastic to the substrate using materials such as thread, yarn, or adhesive in a sewing, weaving, or adhesive process.

For some time, those in the art have been attempting to form elastomeric resins into nonwoven elastomeric materials. For example, attempts have been made to form nonwoven elastomeric webs utilizing elastomeric resins, such as various polystyrene/poly(ethylenebutylene)/polystyrene elastomeric block copolymers. One problem associated with such elastomeric resins, however, is that such elastomeric resins are generally too viscous to be extruded alone without substantial melt fracture of the product.

Thus, many such elastomeric resins need to be blended with a fatty chemical, such as stearic acid, prior to extrusion so as to overcome the viscosity problem. However, physical properties of the product obtained by this process, for example, a nonwoven mat of meltblown fibers, are typically unsatisfactory. After formation of the nonwoven web, substantially all the fatty chemical may be leached out of the nonwoven web of extruded microfibers by soaking the web in alcohols having a good ability to solubilize the fatty chemical utilized.

In order to overcome the above-stated viscosity problems, it is known to form elastomeric block copolymer materials into nonwoven elastomeric products by providing extrudable compositions which are blends of a block copolymer and a processing aid, such as a polyolefin. When blended with the block copolymer and subjected to appropriate elevated pressure and elevated temperature conditions, the processing aid is extrudable in blended form with the block copolymer. The presence of the processing aid in the blend generally serves to reduce the viscosity of the composition as compared to the viscosity of the pure block copolymer and, thus, enhances the extrudability of the composition. However, the use of such processing aids typically negatively affects the elastic properties of the prepared nonwoven elastomeric product as compared to the elastic properties of a nonwoven elastomeric product prepared from a pure block copolymer.

Thus, a void exists with respect to extrudable compositions for forming nonwoven elastomeric materials that can be easily manufactured and that have desirable elastic properties. Furthermore, a void exists with respect to such nonwoven elastomeric materials which can be used to impart elastomeric properties to a composite laminate.

SUMMARY OF THE INVENTION

The present invention concerns a nonwoven elastomeric material combining both desired elastic and adhesive properties that is also highly machine processable.

One aspect of the present invention concerns a nonwoven elastomeric material prepared from a thermoplastic, elastomeric composition. The composition comprises effective amounts of a block copolymer which comprises an elastomeric midblock portion and a thermoplastic endblock portion, a first tackifying resin substantially compatible with and substantially associated with the elastomeric midblock portion, and a second tackifying resin substantially compatible with and substantially associated with the thermoplastic endblock portion, wherein the nonwoven elastomeric material exhibits desired elastic and adhesive properties.

One embodiment of such a nonwoven elastomeric material is prepared from a thermoplastic, elastomeric composition. The composition comprising:

a. from about 45 to about 75 weight percent of a block copolymer which comprises an elastomeric midblock portion and a thermoplastic endblock portion;

b. from about 10 to about 40 weight percent of a first tackifying resin substantially compatible with and substantially associated with the elastomeric midblock portion; and c. from about 10 to about 35 weight percent of a second tackifying resin substantially compatible with and substantially associated with the thermoplastic endblock portion, wherein all weight percents are based on the total amount of the elastomeric block copolymer, the first tackifying resin, and the second tackifying resin present in the thermoplastic, elastomeric composition; and wherein the nonwoven elastomeric material exhibits the following properties:

i. an Initial Modulus value of from about $20 \times 10^6$ to about $80 \times 10^6$ dynes per square centimeter;

ii. a Stress at 50 Percent Extension value of from about $3 \times 10^6$ to about $10 \times 10^6$ dynes per square centimeter;

iii. a Stress Relaxation value of less than about 35 percent; and iv. a Peel Force value that is less than about 200 grams per 25.4 millimeter width.

In another aspect, the present invention concerns a composite laminate comprising a nonwoven elastomeric material prepared from a thermoplastic, elastomeric composition disclosed herein, wherein the nonwoven elastomeric material exhibits desired elastic and adhesive properties.

One embodiment of such a composite laminate comprises a substrate attached to a nonwoven elastomeric material prepared from a thermoplastic, elastomeric composition disclosed herein, wherein the nonwoven elastomeric material exhibits desired elastic and adhesive properties.

In another aspect, the present invention concerns a disposable absorbent product comprising a nonwoven sheet prepared from a thermoplastic, elastomeric composition disclosed herein, wherein the nonwoven sheet exhibits desired elastic and adhesive properties.

One embodiment of such a disposable absorbent product comprises a liquid-permeable topsheet, a backsheet attached to the liquid-permeable topsheet, an absorbent structure positioned between the topsheet and the backsheet, and a nonwoven sheet positioned between the topsheet and the backsheet, wherein the nonwoven sheet is prepared from a thermoplastic, elastomeric composition disclosed herein and the nonwoven sheet exhibits desired elastic and adhesive properties.

DETAILED DESCRIPTION OF THE PREFERRED EMBODIMENTS

Figure 1:
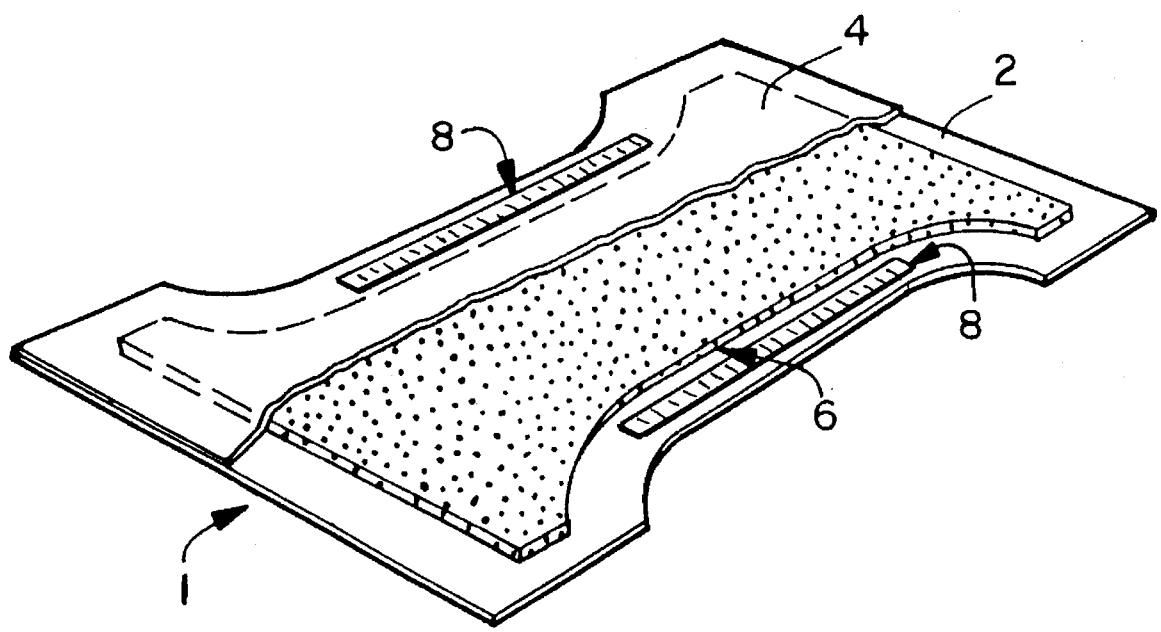
FIG. 1 represents a disposable diaper according to the present invention.

The present invention, in one aspect, concerns a nonwoven elastomeric material that exhibits desired elastic and adhesive properties and is prepared from a thermoplastic, elastomeric composition. The thermoplastic, elastomeric composition generally comprises a block copolymer which comprises an elastomeric midblock portion and a thermoplastic endblock portion, a first tackifying resin substantially compatible with and substantially associated with the elastomeric midblock portion, and a second tackifying resin substantially compatible with and substantially associated with the thermoplastic endblock portion. Such a thermoplastic, elastomeric composition is relatively easy to process and form into useful nonwoven elastomeric materials. Moreover, such nonwoven elastomeric materials have been found to be able to exhibit elastic properties that are substantially similar to a nonwoven elastomeric material that is prepared from an essentially pure block copolymer composition.

As used herein, the terms "elastic" and "elastomeric" are used interchangeably to mean that property of any material which, upon application of a biasing force, permits that material to be stretchable to a stretched, biased length which is at least about 125 percent, that is about 1.25 times, its relaxed, unbiased length, and that will cause the material to recover at least 40 percent of its elongation upon release of the stretching, elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, and many of these will recover to substantially their original relaxed length upon release of the stretching, elongating force. This latter class of materials is generally beneficial for purposes of the present invention.

The term "recover" relates to a contraction of a stretched material upon termination of a biasing force following stretching of the material by application of the biasing force. For example, if a material having a relaxed, unbiased length of one (1) inch were elongated 50 percent by stretching to a length of 1.5 inches, the material would have been elongated 50 percent and would have a stretched length that is 150 percent of its relaxed length. If this exemplary stretched material contracted, that is, recovered to a length of 1.1 inches after release of the biasing and stretching force, the material would have recovered 80 percent (0.4 inch) of its elongation.

As used herein, the term "nonwoven" is intended to mean that the elastomeric material has been formed without the use of a weaving process.

The nonwoven elastomeric material may be in the form of a film or sheet, a fibrous web, threads, fibers, or the like. A nonwoven fibrous web generally has the structure of individual fibers or threads which are interlaid but not in an identifiable, repeatable manner. Nonwoven webs are known to be able to be prepared by a variety of processes such as, for example, meltblowing processes, spunbonding processes, film aperturing processes, and staple fiber carding processes. Nonwoven webs generally have an average basis weight of not more than about 300 grams per square meter and, suitably, have an average basis weight from about 3 to about 100 grams per square meter.

A nonwoven film generally has the structure of a continuous sheet of material with no identifiable, individual fibers or the like. Nonwoven films are known to be able to be prepared by a variety of processes such as, for example, extrusion processes.

A nonwoven thread or fiber generally has the structure wherein in the length is at least about 10 times greater than the width or radius. Such nonwoven threads or fibers may be shaped or essentially round. Nonwoven threads or fibers are known to be able to be prepared by a variety of processes such as, for example, extrusion processes.

As used herein, the term "thermoplastic" is meant to describe a material that softens when exposed to heat and which substantially returns to its original condition when cooled to room temperature.

In general, a nonwoven elastomeric material with desirable elastic properties may be prepared from a composition that comprises essentially only a block copolymer. However, such a composition will generally be very difficult to process because of a high viscosity. In order to improve the processability of a pure block copolymer composition, a processing aid or aids may be added to reduce the viscosity of the composition during processing. One problem with many processing aids, however, is that after processing of the composition has occurred, the processing aid generally associates with either the elastomeric midblock portion or the thermoplastic endblock portion of the block copolymer or, otherwise, generally negatively affects the desired elastic and/or adhesive properties of the prepared nonwoven sheet.

It is, therefore, desirable to use a combination of processing aids, such as both midblock and endblock portion associating tackifying resins, with a block copolymer to improve the processability of the composition while at the same time being able to prepare a nonwoven elastomeric material from the composition that exhibits both desired elastic and adhesive properties.

A number of block copolymers can be used to prepare the thermoplastic, elastomeric compositions useful in preparing the nonwoven elastomeric material of this invention. Such block copolymers generally comprise an elastomeric midblock portion and a thermoplastic endblock portion. The block copolymers used in this invention generally have a three-dimensional physical crosslinked structure below the endblock portion glass transition temperature ($T_g$) and are elastomeric. The block copolymers are also thermoplastic in the sense that they can be melted above the endblock $T_g$, formed, and resolidified several times with little or no change in physical properties (assuming a minimum of oxidative degradation).

One way of synthesizing such block copolymers is to polymerize the thermoplastic endblock portions separately from the elastomeric midblock portions. Once the midblock and endblock portions have been separately formed, they can be linked. Typically, midblock portions can be obtained by polymerizing di- and tri-unsaturated $C_4$–$C_{10}$ hydrocarbons such as, for example, dienes such as butadiene, isoprene, and the like, and trienes such as 1,3,5-heptatriene, and the like. When an endblock portion A is joined to a midblock portion B, an A-B block copolymer unit is formed, which unit can be coupled by various techniques or with various coupling agents C to provide a structure such as A-B-A, which is believed to comprise two A-B blocks joined together in a tail-to-tail A-B-C-B-A arrangement. By a similar technique, a radial block copolymer can be formed having the formula $(A-B)_nC$, wherein C is the hub or central, polyfunctional coupling agent and n is a number greater than 2. Using the coupling agent technique, the functionality of C determines the number of A-B branches.

Endblock portion A generally comprises a poly(vinylarene), such as polystyrene, having an average molecular weight between 1,000 and 60,000. Midblock portion B generally comprises a substantially amorphous polyolefin such as polyisoprene, ethylene/propylene polymers, ethylene/butylene polymers, polybutadiene, and the like, or mixtures thereof, having an average molecular weight between about 5,000 and about 450,000. The total molecular weight of the block copolymer is suitably about 10,000 to about 500,000 and more suitably about 200,000 to about 300,000. Any residual unsaturation in the midblock portion of the block copolymer can be hydrogenated selectively so that the content of olefinic double bonds in the block copolymers can be reduced to a residual proportion of less than 5 percent and suitably less than about 2 percent. Such hydrogenation tends to reduce sensitivity to oxidative degradation and may have beneficial effects upon elastomeric properties.

Suitable block copolymers used in this invention comprise at least two substantially polystyrene endblock portions and at least one substantially ethylene/butylene midblock portion. Ethylene/butylene typically comprises the major amount of the repeating units in such a block copolymer and can constitute, for example, 70 percent by weight or more of the block copolymer. The block copolymer, if radial, can have three or more arms, and good results can be obtained with, for example, four, five, or six arms. The midblock portion can be hydrogenated, if desired.

Linear block copolymers, such as A-B-A, A-B-A-B-A, or the like, are suitably selected on the basis of endblock content, large endblocks being preferred. For polystyrene-ethylene/butylene-polystyrene block copolymers, a styrene content in excess of about 10 weight percent is suitable, such as between about 12 to about 30 weight percent. With higher styrene content, the polystyrene endblock portions generally have a relatively high molecular weight. A commercially available example of such a linear block copolymer is a styrene-ethylene/butylene-styrene block copolymer which contains about 13 weight percent styrene units, and essentially the balance being ethylene/butylene units, commercially available from the Shell Chemical Company, under the trade designation KRATON G1657 elastomeric resin. Typical properties of KRATON G1657 elastomeric resin are reported to include a tensile strength of 3400 pounds per square inch ($2\times10^6$ kilograms per square meter), a 300 percent modulus of 350 pounds per square inch ($1.4\times10^5$ kilograms per square meter), an elongation of 750 percent at break, a Shore A hardness of 65, and a Brookfield viscosity, when at a concentration of 25 weight percent in a toluene solution, of about 4200 centipoise at room temperature.

The block copolymer will generally be present in the thermoplastic, elastomeric composition of the present invention in an amount beneficially from about 45 to about 75 weight percent, suitably from about 50 to about 65 weight percent, and more suitably from about 60 to about 65 weight percent of the total weight of the block copolymer, a first tackifying resin substantially compatible with and substantially associated with the elastomeric midblock portion of the block copolymer, and a second tackifying resin substantially compatible with and substantially associated with the thermoplastic endblock portion of the block copolymer present in the thermoplastic, elastomeric composition. The block copolymer should be used in the thermoplastic, elastomeric composition in an amount effective to achieve the desired elastic and adhesive properties of a prepared nonwoven elastomeric material.

It has been found that, by using certain processing aids, specifically a first tackifying resin substantially compatible with and substantially associated with the elastomeric midblock portion of the block copolymer, and a second tackifying resin substantially compatible with and substantially associated with the thermoplastic endblock portion of the block copolymer, it is possible to prepare a thermoplastic, elastomeric composition that is easily processed into nonwoven elastomeric materials that have elastic properties that are similar to a nonwoven elastomeric material prepared from an essentially pure block copolymer composition.

A variety of resins with tackifying properties are substantially compatible with and substantially associate with the polymer midblock portions of the block copolymer, including those midblock portions which have been hydrogenated so as to become virtually identical, chemically and physically, to polymerized mono-olefins, such as polyethylene, polypropylene, polybutylene, or the like.

As used herein, the term "substantially compatible with and substantially associated with", and other related terms, are meant to indicate that a particular tackifying resin, when mixed with a block copolymer comprising an elastomeric midblock portion and a thermoplastic endblock portion, exists in essentially close and permanent association for an indefinite period with a particular portion of the block copolymer. As such, the midblock associating tackifying resins tend to associate with the elastomeric midblock portion of the block copolymer and, thereby, tend to extend or build up these elastomeric midblock portions. In contrast, the endblock associating tackifying resins tend to associate with the thermoplastic endblock portion of the block copolymer and, thereby, tend to extend or build up these thermoplastic endblock portions.

Both natural and synthetic, essentially hydrocarbon resins can be used as midblock associating tackifying resins provided that these resins contain substantial aliphatic character, which character can be provided by the aliphatic portion of rosin acids, repeating isoprene or other diene units, such as by polymerized 1,3-pentadiene, polymerized cycloaliphatics, and the like.

Essentially hydrocarbon resins are preferred for use as the midblock associating tackifying resins, particularly the so-called aliphatic and hydrogenated resins. These polymers can be natural or synthetic and can be copolymers, such as terpenes or the like.

All resins do not necessarily work with equal effectiveness as a midblock associating tackifying resin in the present invention. Suitable midblock associating tackifying resins include synthetic terpenes having a softening point of about 80° C. to about 115° C.

An example of a midblock associating tackifying resin useful in the present invention is made from monomers of styrene or alpha methyl styrene, or a copolymer-of these, which can be hydrogenated partially or completely, commercially available from the Hercules Corporation under the trade designation REGALREZ 1126. Typical properties of REGALREZ 1126 are reported to include a melting point of between about 122° C. to about 130° C. and a glass transition temperature of about 65° C.

The first tackifying resin, substantially compatible with and substantially associated with the elastomeric midblock portion of the block copolymer, will generally be present in the thermoplastic, elastomeric composition of the present invention in an amount beneficially from about 10 to about 45 weight percent, suitably from about 10 to about 30 weight percent, and more suitably from about 15 to about 20 weight percent of the total weight of a block copolymer, the first tackifying resin substantially compatible with and substantially associated with the elastomeric midblock portion of the block copolymer, and a second tackifying resin substantially compatible with and substantially associated with the thermoplastic endblock portion of the block copolymer present in the thermoplastic, elastomeric composition. The first tackifying resin, substantially compatible with and substantially associated with the elastomeric midblock portion of the block copolymer, should be used in the thermoplastic, elastomeric composition in an amount effective to achieve the desired elastic and adhesive properties of a prepared nonwoven elastomeric material.

Tackifying resins with aromatic character tend to associate with the endblock portions of the block copolymer. Suitable endblock associating tackifying resins include coumarone-indenes, polystyrene, poly-alpha-methylstyrene, polyindenes, and other resins containing monocyclic or polycyclic aromatic groups.

Examples of an endblock associating tackifying resin useful in the present invention include an intermediate molecular weight, nonpolar, thermoplastic hydrocarbon prepared from styrene monomer, commercially available from the Hercules Corporation, under the trade designation PICCOLASTIC D-125, and a similar, but lower molecular weight, material under the trade designation PICCOLASTIC A-75.

It is desirable that the endblock associating tackifying resin have a glass transition temperature and a softening point above those of the end block portion and of the midblock associating tackifying resin. For example, it would generally not be desirable for the glass transition and for significant heat softening to occur below about 70° C. Thus, endblock associating tackifying resins with somewhat higher molecular weights and softening points above about 75° C. are typically selected. Suitable resins with softening points within the range of about 75° C. to about 160° C. are commercially available.

The second tackifying resin, substantially compatible with and substantially associated with the thermoplastic endblock portion of the block copolymer, will generally be present in the thermoplastic, elastomeric composition of the present invention in an amount beneficially from about 10 to about 35 weight percent, suitably from about 10 to about 30 weight percent, and more suitably from about 12 to about 27 weight percent of the total weight of a block copolymer, a first tackifying resin substantially compatible with and substantially associated with the elastomeric midblock portion of the block copolymer, and the second tackifying resin substantially compatible with and substantially associated with the thermoplastic endblock portion of the block copolymer present in the thermoplastic, elastomeric composition. The second tackifying resin, substantially compatible with and substantially associated with the thermoplastic endblock portion of the block copolymer should be used in the thermoplastic, elastomeric composition in an amount effective to achieve the desired elastic and adhesive properties of a prepared nonwoven elastomeric material.

While the principal components of the thermoplastic, elastomeric composition of the present invention have been described in the foregoing, such composition is not limited thereto and can include other components not adversely effecting the nonwoven elastomeric material having the desired properties. Exemplary materials which could be used as additional components would include, without limitation, pigments, antioxidants, stabilizers, surfactants, waxes, flow promoters, solid solvents, particulates, and materials added to enhance processability of the composition.

It is desirable that the nonwoven elastomeric material of the present invention exhibit both desirable elastic and adhesive properties. In general, it is desired that the nonwoven elastomeric material exhibit elastic and adhesive properties that are similar to those that would be achieved if an essentially pure block copolymer composition were used to prepare the nonwoven elastomeric material.

Typical elastic materials generally comprise a crosslinked three-dimensional structure which functions as a reversible energy storing network. Stress applied to the substance results in a strain or deformation of the three-dimensional network which stores energy, applied during stress, which can be spontaneously substantially recovered upon the removal of the stress.

Adhesive materials, in contrast to elastic-materials, generally require a different set of properties. Upon the application of stress or force to, for example, a pressure sensitive adhesive, the adhesive must deform in order to come into intimate contact through viscous flow with the surface of a substrate in order to form adhesive bonds by van der Waals attraction. In order to preserve the adhesive bond, upon removal Of the stress or pressure, the adhesive material must not recover from the deformation. Substances that are pressure sensitive adhesives exhibit viscous flow and therefore inherently do not substantially recover from such deformation. Elastic materials therefore generally-have minimal adhesive properties and pressure sensitive adhesives generally have minimal elastic properties.

It is therefore desired in the present invention that the use of the midblock and endblock associating resins do not substantially increase the adhesive properties of the prepared nonwoven elastomeric material, since such an increase in the adhesive properties generally results in a corresponding decrease in the elastic properties of the prepared nonwoven elastomeric material.

Elastic properties desired of the nonwoven elastomeric material of the present invention include exhibiting effective Initial Modulus, Stress at 50 Percent Extension, and Stress Relaxation values, described herein.

The Initial Modulus value of a nonwoven elastomeric material is meant to represent the amount of force initially needed to stretch the nonwoven elastomeric material and, thus, generally represents the stiffness of the nonwoven elastomeric material. It is desired that the nonwoven elastomeric material not exhibit an Initial Modulus that is too low such that the nonwoven elastomeric material has too soft of a feel to a user. Also, it is desired that the nonwoven elastomeric material not exhibit an Initial Modulus that is too high such that the nonwoven elastomeric material requires too much initial force for the nonwoven elastomeric material to deform during use.

Thus, the nonwoven elastomeric material of the present invention exhibits an Initial Modulus value that is beneficially from about $20 \times 10^6$ to about $80 \times 10^6$ dynes per square centimeter, suitably from about $20 \times 10^6$ to about $60 \times 10^6$ dynes per square centimeter, and more suitably from about $20 \times 10^6$ to about $50 \times 10^6$ dynes per square centimeter, as measured according to the methods described in the Test Procedures section herein.

The Stress at 50 Percent Extension value of a nonwoven elastomeric material is meant to represent the amount of force exerted by the nonwoven elastomeric material when it is elongated 50 percent by stretching. It is desired that the nonwoven sheet not exhibit a Stress at 50 Percent Extension value that is too low, since such may result in the slipping or falling, for example, of a disposable absorbent product that includes the nonwoven elastomeric material. Also, it is desired that the nonwoven sheet not exhibit a Stress at 50 Percent Extension value that is too high, since such may cause the nonwoven sheet to exert too much force, for example, against a wearer of a disposable absorbent product including the nonwoven sheet, thus, causing redmarking on the wearer.

Thus, the nonwoven elastomeric material of the present invention exhibits an Stress at 50 Percent Extension value that is beneficially from about $3 \times 10^6$ to about $10 \times 10^6$ dynes per square centimeter, suitably from about $3 \times 10^6$ to about $8 \times 10^6$ dynes per square centimeter, and more suitably from about $6 \times 10^6$ to about $8 \times 10^6$ dynes per square centimeter, as measured according to the methods described in the Test Procedures section herein.

The Stress Relaxation value of a nonwoven elastomeric material is meant to represent the stress value exhibited by a nonwoven elastomeric material when it is allowed to relax for 20 minutes while elongated at 50 percent extension. It is desired that the nonwoven elastomeric material not exhibit a Stress Relaxation value that is too high, since such will indicate that the nonwoven elastomeric material will not have much tension left in it and will result in the slipping or falling, for example, of a disposable absorbent product that includes the nonwoven elastomeric material.

Thus, the nonwoven elastomeric material of the present invention exhibits a Stress Relaxation value that is beneficially less than about 35 percent, suitably less than about 30 percent, and more suitably less than about 25 percent, as measured according to the methods described in the Test Procedures section herein.

As used herein, the term "adhesive" is used to mean that property of any material that allows the material to bond together substrates by surface attachment. Such bonding may result from the application of a pressure force, in the case of a pressure sensitive adhesive material, or a sufficiently high temperature, in the case of a hot-melt adhesive, to contact and bond the adhesive material to a substrate.

Adhesive properties desired of the nonwoven elastomeric material of the present invention include effective Peel Force values.

The Peel Force value of a nonwoven elastomeric material is meant to represent the adhesive bond strength of the material. It is desired that the nonwoven elastomeric material not exhibit a Peel Force value that is too high, since such will generally indicate that the nonwoven elastomeric material is too self-adhering and will, thus, generally have poor elastic properties.

The Tensile Strength value of a nonwoven elastomeric material is meant to represent the cohesive strength of the nonwoven elastomeric material. It is desired that the nonwoven elastomeric material not exhibit a Tensile Strength value that is too low, since such will indicate that the nonwoven elastomeric material is very soft and viscous.

Thus, the nonwoven elastomeric material of the present invention exhibits a Peel Force value that is beneficially less than about 200 grams per 25.4 millimeter width, suitably less than about 150 grams per 25.4 millimeter width, and more suitably less than about 80 grams per 25.4 millimeter width, as measured according to the methods described in the Test Procedures section herein.

Generally, the nonwoven elastomeric material of the present invention exhibits a Peel Force value that is beneficially less than about 30 percent, suitably less than about 20 percent, and more suitably less than about 10 percent, of the Tensile Strength value of the nonwoven elastomeric material, as measured according to the methods described in the Test Procedures section herein.

The nonwoven elastomeric material of the present invention may generally be of any size or dimension as long as the nonwoven elastomeric material exhibits the desired elastic and adhesive properties as described herein.

The nonwoven elastomeric material of the present invention may also be used or combined with other nonwoven elastomeric materials, with the nonwoven elastomeric material of the present invention being used as a separate layer or as an individual zone or area within a larger, composite nonwoven elastomeric material. The nonwoven elastomeric materials of the present invention may be combined with other nonwoven elastomeric materials by methods well known to those skilled in the art, such as by using adhesives, or simply by layering the different materials together and holding together the composite materials with, for example, stitching or by application of heat and pressure.

In another aspect of the present invention, it is desired to use a nonwoven elastomeric material to prepare an elastic composite comprising at least one gatherable material attached to at least one nonwoven elastomeric material.

Such an elastic composite may be prepared by tensioning the nonwoven elastomeric material so as to elongate it, then attaching the elongated nonwoven elastomeric material to at least one gatherable material, and then relaxing the elastic composite so that the gatherable material is gathered by relaxing the nonwoven elastomeric material. Typical conditions for attaching the nonwoven elastomeric material to the gatherable material include overlaying the nonwoven elastomeric and the gatherable materials and applying heat and/or pressure to the overlaid materials so as to create bonding sites between the overlaid materials.

Various gatherable materials can be utilized in forming the elastic composite. Such gatherable materials can include, but are not limited to, non-elastic fibrous webs, such as carded non-elastic polyester or non-elastic polypropylene fibrous webs, spunbonded non-elastic polyester or polypropylene non-elastic fibrous webs, non-elastic cellulosic fibrous webs, polyamide fibrous webs, and blends of two or more of the foregoing. Particularly suitable is using the gatherable material as outer cover layers with the nonwoven elastomeric material sandwiched as an intermediate layer between the gatherable material layers. Basis weights for the elastic composite are beneficially between about 4 to about 100 grams per square meter and suitably between about 6 to about 30 grams per square meter.

In one embodiment of the present invention, a disposable absorbent product is provided, which disposable absorbent product comprises a liquid-permeable topsheet, a backsheet attached to the topsheet, an absorbent structure positioned between the topsheet and the backsheet, and a nonwoven elastomeric material of the present invention wherein the nonwoven elastomeric material is positioned between the topsheet and the backsheet.

While one embodiment of the invention will be described in terms of the use of a nonwoven elastomeric material in an infant diaper, it is to be understood that the nonwoven elastomeric material is equally suited for use in other disposable absorbent products known to those skilled in the art.

FIG. 1 illustrates a disposable diaper 1 according to one embodiment of the present invention. Disposable diaper 1 includes a backsheet 2, a topsheet 4, an absorbent structure 6 positioned between the backsheet 2 and the topsheet 4, and a nonwoven elastomeric material 8 positioned between the backsheet 2 and the topsheet 4. Nonwoven elastomeric material 8 is a nonwoven elastomeric material according to the present invention. Specifically, in the illustrated embodiment, nonwoven elastomeric material 8 is used as a pair of leg elastics positioned on either side of the absorbent 6 of the diaper.

Other uses of the nonwoven elastomeric material in a disposable absorbent product include waist elastics or side panels as, for example, in a child's training pant.

Those skilled in the art will recognize materials suitable for use as the topsheet and backsheet. Exemplary of materials suitable for use as the topsheet are liquid-permeable materials, such as spunbonded polypropylene or polyethylene having a basis weight of from about 15 to about 25 grams per square meter. Exemplary of materials suitable for use as the backsheet are liquid-impervious materials, such as polyolefin films, as well as vapor-pervious materials, such as microporous polyolefin films.

Disposable absorbent products, according to all aspects of the present invention, are generally subjected during use to multiple insults of a body liquid. Accordingly, the disposable absorbent products are desirably capable of absorbing multiple insults of body liquids in quantities to which the absorbent products and structures will be exposed during use. The insults are generally separated from one another by a period of time.

Test Procedures

Figure 2:
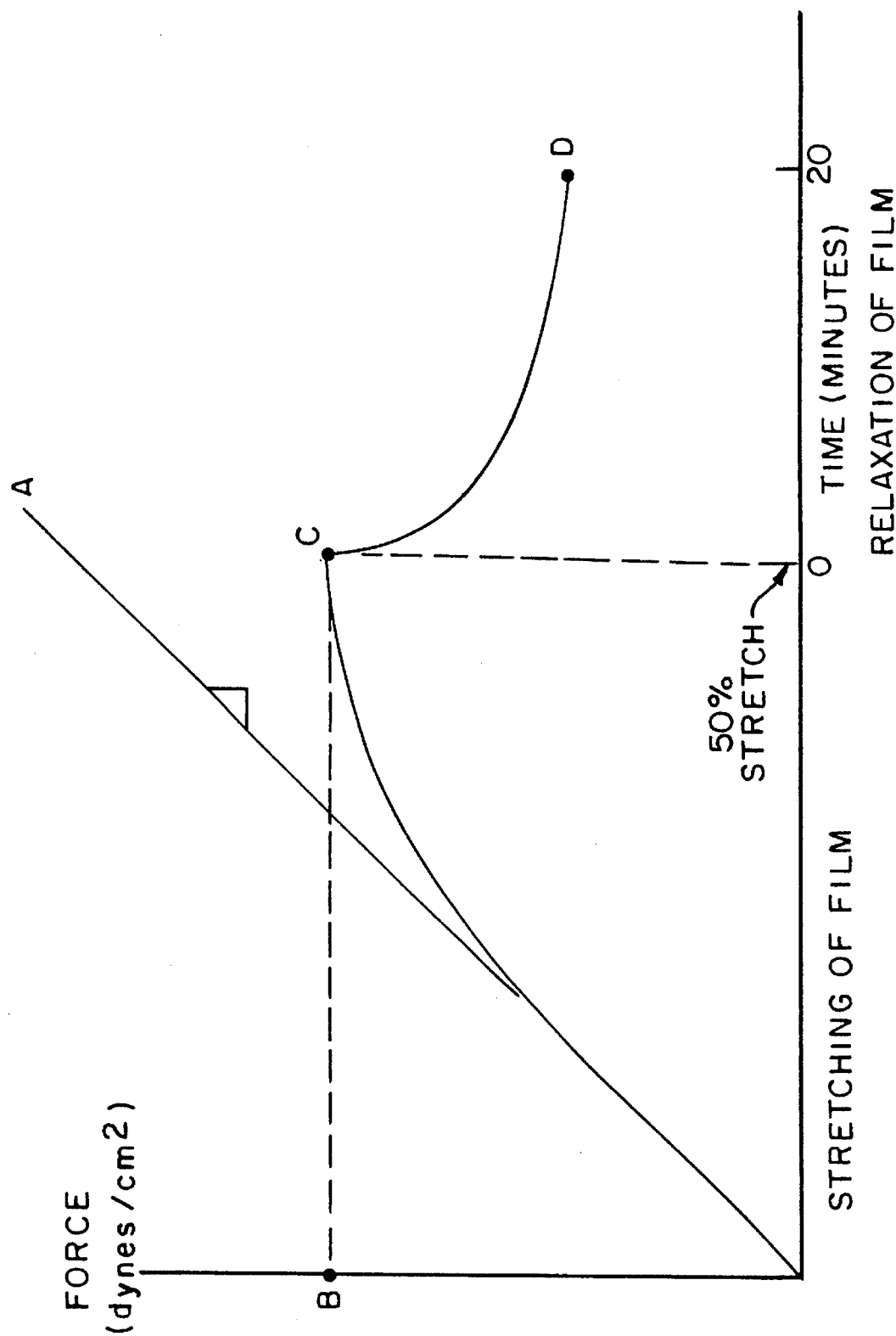
FIG. 2 illustrates a representative plot of the stress-strain force measurements of a nonwoven elastomeric material sample stretched using a tensile tester.

A commercial tensile tester was used to stretch, at a stretch rate of about 300 millimeters per minute and at a temperature of about 23° C., a nonwoven elastomeric material sample, in the form of a film, that was about 3 inches (about 7.6 centimeters) wide, about 100 millimeters long, and about 0.016 inch (0.04 centimeter) thick, to a stretched extension of about 50 percent of original length, or about 50 millimeters, such that the stretched film had a total stretched length of about 150 millimeters. During such stretching of the film sample, the stretch force, in grams, was measured. Once the desired stretched length was obtained, the film sample was held at the 50 percent stretched extension for about 20 minutes. During these 20 minutes, the stress relaxation force of the film sample was measured. A representative plot of a stress-strain force measurement is shown in FIG. 2. The mechanical properties of the film sample were determined as follows:

Initial Modulus:

The Initial Modulus value, in dynes per square centimeter, was taken to be the slope of a tangent (line A in FIG. 2) drawn to the curve of the stress/strain measurements at the origin (0 percent stretch), normalized with respect to the area of the cross-section of the film sample.

Stress at 50 Percent Extension:

The Stress at 50 Percent Extension value, in dynes per square centimeter, was determined by simply reading the force value at 50 percent extension of the film sample (point B in FIG. 2), normalized with respect to the area of the cross-section of the film sample.

Stress Relaxation:

The Stress Relaxation value, recorded as a percentage, was determined by measuring the difference in stress force for the 50 percent extended film sample between when the sample first reaches the 50 percent stretched extension (point C in FIG. 2), and then after the 20 minute relaxation time period (point D in FIG. 2), dividing by the initial stress for the 50 percent extended film sample (point C in FIG. 2), and then multiplying by 100 percent.

Peel Force:

The Peel Force value, in grams per 25.4 millimeter width, is a measurement of the 180° peel force adhesive bond strength of a film sample and is measured according to the standardized test method PSTC-1, revised as of August 1989, incorporated herein by reference.

Tensile Strength:

The Tensile Strength value, in dynes per square centimeter, is a measurement of the stress exerted by a film sample at its point of 500 percent extension, normalized with respect to the initial area of cross section, in square centimeters. A commercial tensile tester was used to stretch, at a stretch rate of about 300 millimeters per minute, a film sample that was about 3 inches (about 7.6 centimeters) wide and about 100 millimeters long until the film sample was extended 500 percent from its original, relaxed length.

EXAMPLE 1

Samples were prepared of compositions that could be extruded into a film for evaluation. In the samples, the block copolymer used was a linear styrene-ethylene/butylene-styrene block copolymer, which contains about 13 weight percent styrene units and, essentially, the balance being ethylene/butylene units, commercially available in pellet form from the Shell Chemical Company under the trade designation KRATON G1657. The midblock associating tackifier used was made from monomers of styrene or alpha methyl styrene, or a copolymer of these, which can be hydrogenated partially or completely, commercially available in the form of flakes from the Hercules Corporation under the trade designation REGALREZ 1126. The endblock associating tackifier used was an intermediate molecular weight, nonpolar, thermoplastic hydrocarbon prepared from styrene monomer, commercially available in the form of flakes from the Hercules Corporation under the trade designation PICCOLASTIC D-125.

A first control sample was prepared that included only the block copolymer. A second control sample was prepared that included the block copolymer, the midblock tackifier, and a processing aid that was a polyethylene wax, with a meltflow index of about 2000, commercially available from the Quantum Chemical Company under the trade designation NA 601.

The samples were prepared by using an internal mixer fitted with a double blade mixer, available from the C. W. Brabender Company. The temperature of mixing was about 370° F. (about 190° C.) and the speed of rotation of the mixer was about 10 to about 20 revolutions per minute. The pellets of block copolymer were first added to the internal mixer and were mixed for about 20 minutes until they melted. The tackifying resins and/or the processing aid were then slowly added to the melted block copolymer and mixed for an additional 20 minutes. The speed of mixing was adjusted between about 10 to about 20 revolutions per minute for uniform mixing as determined by visual inspection. The mixed composition was then allowed to cool to room temperature (about 23° C.), during which time the composition solidified to a rubbery mass. The solid mass was then cut into small pieces using a hot knife.

A compression molding press, available from the Dake Corporation, was used along with a custom-prepared mold having the dimensions of about 6 inches (about 15 centimeters) wide, about 6 inches (about 15 centimeters) long, and about 0.02 inch (0.05 centimeter) deep to prepare films of the compositions. About 20 grams of a composition was placed into the mold. The mold was then placed between two layers of release liners and two flat plates. The entire mold assembly was then placed in the compression molding press and maintained at a temperature of about 370° F. (about 190° C.) for about 1 hour without any pressure on the mold. During this time, the composition had melted in the mold, between the two release liners. A pressure of between about 100 and about 800 pounds per square inch was then applied to the mold. The heaters were then shut off and the sample was left in the compression molding press, under pressure for about 10 hours, allowing the sample to slowly reach room temperature (about 23° C.) in order to achieve an equilibrium morphology. The prepared film was then removed from the mold and left at room temperature for about 2 days before evaluating the properties of the film.

The film samples were then evaluated for elastic and adhesive properties using the test procedures described in the Test Methods section. The compositions and properties of the Samples are shown in Table 1.

Those skilled in the art will recognize that the present invention is capable of many modifications and variations without departing from the scope thereof. Accordingly, the detailed description and examples set forth above are meant to be illustrative only and are not intended to limit, in any manner, the scope of the invention as set forth in the appended claims.

and wherein the nonwoven elastomeric material exhibits the following properties:
  i. an Initial Modulus value of from about $20 \times 10^6$ to about $80 \times 10^6$ dynes per square centimeter;
  ii. a Stress at 50 Percent Extension value of from about $3 \times 10^6$ to about $10 \times 10^6$ dynes per square centimeter;
  iii. a Stress Relaxation value of less than about 35 percent; and
  iv. a Peel Force value that is less than about 200 grams per 25.4 millimeter width.

2. The nonwoven elastomeric material of claim 1 wherein the block copolymer is a linear block copolymer or a radial block copolymer.

3. The nonwoven elastomeric material of claim 1 wherein the thermoplastic endblock portion of the block copolymer comprises a poly(vinylarene).

4. The nonwoven elastomeric material of claim 3 wherein the thermoplastic endblock portion of the block copolymer comprises a polystyrene.

5. The nonwoven elastomeric material of claim 1 wherein the elastomeric midblock portion of the block copolymer comprises an amorphous polyolefin.

6. The nonwoven elastomeric material of claim 5 wherein the elastomeric midblock portion of the block copolymer comprises a polyisoprene, an ethylene/propylene, an ethylene/butylene, or a polybutadiene polymer.

TABLE 1

| | COMPOSITION (weight %) | | | | PROPERTIES | | | |
| --- | --- | --- | --- | --- | --- | --- | --- | --- |
| | Block Copolymer | Midblock Resin | Endblock Resin | PolyEth Wax | Initial Modulus ($\times 10^6$ dynes/cm$^2$) | Stress at 50% extension ($\times 10^6$ dynes/cm$^2$) | Stress Relaxation (%) | Peel Force (grams/25.4 mm) |
| Control 1* | 100 | — | — | — | 16 | 6 | 23.5 | 20 |
| Control 2* | 63 | 17 | — | 20 | 91.2 | 11.3 | 33 | 70 |
| Sample 1 | 63 | 17 | 20 | — | 31.2 | 6.7 | 24 | 60 |
| Sample 2 | 50 | 25 | 25 | — | 38.2 | 6.9 | 28 | 10 |
| Sample 3 | 55 | 17 | 28 | — | 30.9 | 6.2 | 25 | 10 |
| Sample 4 | 63 | 25 | 12 | — | 29.8 | 6.1 | 24.5 | 16 |
| Sample 5 | 70 | 15 | 15 | — | 29.1 | 6.7 | 23.4 | 45 |
| Sample 6 | 63 | 10 | 27 | — | 36 | 7.2 | 23.7 | 70 |
| Sample 7 | 55 | 30 | 15 | — | 35 | 6.3 | 27.3 | 12 |
| Sample 8 | 50 | 40 | 10 | — | 31.6 | 5.6 | 30.9 | 17 |
| Sample 9 | 70 | 10 | 20 | — | 29.8 | 7.9 | 27.4 | 55 |
| Sample 10 | 50 | 20 | 30 | — | 46 | 8.3 | 27.8 | 50 |

*Not an example of the present invention.

What is claimed is:

1. A nonwoven elastomeric material prepared from a thermoplastic, elastomeric composition, the composition comprising:
  a. from about 45 to about 75 weight percent of a block copolymer which comprises an elastomeric midblock portion and a thermoplastic endblock portion;
  b. from about 10 to about 40 weight percent of a first tackifying resin substantially compatible with and substantially associated with the elastomeric midblock portion; and
  c. from about 10 to about 35 weight percent of a second tackifying resin substantially compatible with and substantially associated with the thermoplastic endblock portion, wherein all weight percents are based on the total amount of the elastomeric block copolymer, the first tackifying resin, and the second tackifying resin present in the thermoplastic, elastomeric composition;

7. The nonwoven elastomeric material of claim 1 wherein the block copolymer has a total molecular weight between about 10,000 to about 500,000.

8. The nonwoven elastomeric material of claim 1 wherein the thermoplastic endblock portion of the block copolymer comprises a polystyrene, and the elastomeric midblock portion of the block copolymer comprises an ethylene/butylene polymer.

9. The nonwoven elastomeric material of claim 1 wherein the thermoplastic, elastomeric composition comprises from about 50 to about 65 weight percent of the block copolymer.

10. The nonwoven elastomeric material of claim 1 wherein the first tackifying resin comprises an essentially hydrocarbon resin.

11. The nonwoven elastomeric material of claim 10 wherein the first tackifying resin is an aliphatic resin or a hydrogenated resin.

12. The nonwoven elastomeric material of claim 10 wherein the first tackifying resin is prepared from monomers of styrene or alpha methyl styrene.

13. The nonwoven elastomeric material of claim 1 wherein the first tackifying resin has a softening point of between about 80° C. to about 115° C.

14. The nonwoven elastomeric material of claim 1 wherein the thermoplastic, elastomeric composition comprises from about 10 to about 30 weight percent of the first tackifying resin.

15. The nonwoven elastomeric material of claim 1 wherein the second tackifying resin is an aromatic resin.

16. The nonwoven elastomer c material of claim 1 wherein the second tackifying resin is a coumarone-indene polymer, a polystyrene polymer, a poly-alpha-methylstyrene polymer, or a polyindene polymer.

17. The nonwoven elastomer c material of claim 1 wherein the second tackifying resin has a softening point of between about 75° C. to about 160° C.

18. The nonwoven elastomer c material of claim 1 wherein the thermoplastic, elastomeric composition comprises from about 10 to about 30 weight percent of the second tackifying resin.

19. The nonwoven elastomer c material of claim 1 wherein the nonwoven elastomeric material is in the form of a film, a fibrous web, or a thread.

20. The nonwoven elastomer c material of claim 1 wherein the nonwoven elastomeric material exhibits an Initial Modulus value of from about $20\times10^6$ to about $60\times10^6$ dynes per square centimeter.

21. The nonwoven elastomeric material of claim 1 wherein the nonwoven elastomeric material exhibits a Stress at 50 Percent Extension value of from about $3\times10^6$ to about $8\times10^6$ dynes per square centimeter.

22. The nonwoven elastomeric material of claim 1 wherein the nonwoven elastomeric material exhibits a Stress Relaxation value of less than about 30 percent.

23. The nonwoven elastomeric material of claim 1 wherein the nonwoven elastomeric material exhibits a Peel Force value that is less than about 150 grams per 25.4 millimeter width.

24. An elastic composite comprising a gatherable substrate attached to a nonwoven elastomeric material, wherein the nonwoven elastomeric material is prepared from a thermoplastic, elastomeric composition, the composition comprising:
   a. from about 45 to about 75 weight percent of a block copolymer which comprises an elastomeric midblock portion and a thermoplastic endblock portion;
   b. from about 10 to about 40 weight percent of a first tackifying resin substantially compatible with and substantially associated with the elastomeric midblock portion; and
   c. from about 10 to about 35 weight percent of a second tackifying resin substantially compatible with and substantially associated with the thermoplastic endblock portion, wherein all weight percents are based on the total amount of the elastomeric block copolymer, the first tackifying resin, and the second tackifying resin present in the thermoplastic, elastomeric composition; and wherein the nonwoven elastomeric material exhibits the following properties:
   i. an Initial Modulus value of from about $20\times10^6$ to about $80\times10^6$ dynes per square centimeter;
   ii. a Stress at 50 Percent Extension value of from about $3\times10^6$ to about $10\times10^6$ dynes per square centimeter;
   iii. a Stress Relaxation value of less than about 35 percent; and
   iv. a Peel Force value that is less than about 200 grams per 25.4 millimeter width.

25. The elastic composite of claim 24 wherein the gatherable substrate is a non-elastic fibrous web comprising polyester, polypropylene, cellulosic, or polyamide.

26. A disposable absorbent product comprising a liquid-permeable topsheet, a backsheet attached to the liquid-permeable topsheet, an absorbent structure positioned between the liquid-permeable topsheet and the backsheet, and a nonwoven elastomeric material positioned between the liquid-permeable topsheet and the backsheet, wherein the nonwoven elastomeric material is prepared from a thermoplastic, elastomeric composition, the composition comprising:
   a. from about 45 to about 75 weight percent of a block copolymer which comprises an elastomeric midblock portion and a thermoplastic endblock portion;
   b. from about 10 to about 40 weight percent of a first tackifying resin substantially compatible with and substantially associated with the elastomeric midblock portion; and
   c. from about 10 to about 35 weight percent of a second tackifying resin substantially compatible with and substantially associated with the thermoplastic endblock portion, wherein all weight percents are based on the total amount of the elastomeric block copolymer, the first tackifying resin, and the second tackifying resin present in the thermoplastic, elastomeric composition, and wherein the nonwoven elastomeric material exhibits the following properties:
   i. an Initial Modulus value of from about $20\times10^6$ to about $80\times10^6$ dynes per square centimeter;
   ii. a Stress at 50 Percent Extension value of from about $3\times10^6$ to about $10\times10^6$ dynes per square centimeter;
   iii. a Stress Relaxation value of less than about 35 percent; and
   iv. a Peel Force value that is less than about 200 grams per 25.4 millimeter width.

* * * * *